US00PP30753P3

(12) United States Plant Patent
Sakurai

(10) Patent No.: US PP30,753 P3
(45) Date of Patent: Jul. 30, 2019

(54) ***VACCINIUM CORYMBOSUM* L. PLANT NAMED 'RYOKU NH-12'**

(50) Latin Name: ***Vaccinium corymbosum* L.**
Varietal Denomination: RYOKU NH-12

(71) Applicant: NIPPON RYOKUSAN CO., LTD., Matsumoto-shi (JP)

(72) Inventor: Shigetaka Sakurai, Matsumoto (JP)

(73) Assignee: NIPPON RYOKUSAN CO., LTD., Matsumoto-shi (JP)

( * ) Notice: Subject to any disclaimer, the term of this patent is extended or adjusted under 35 U.S.C. 154(b) by 0 days.

(21) Appl. No.: 15/732,725

(22) Filed: Dec. 21, 2017

(65) Prior Publication Data

US 2018/0199482 P1 Jul. 12, 2018

(30) Foreign Application Priority Data

Jan. 4, 2017 (JP) ..... 31724

(51) Int. Cl.
*A01H 5/08* (2018.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — Annette H Para

(74) *Attorney, Agent, or Firm* — Oblon, McClelland, Maier & Neustadt, L.L.P.

(57) ABSTRACT

A new and distinct variety of *Vaccinium corymbosum* L. plant named 'RYOKU NH-12', characterized by having more compact plant size, comparatively early fruit ripening time, comparatively large and uniform fruit size, firmer and lower dehiscent fruits, sweeter fruits, better taste balance of sweetness and acidity, and better taste of fruits, as compared to other *Vaccinium corymbosum* L. varieties.

8 Drawing Sheets

The Latin name of the genus and species of the novel variety disclosed herein is: *Vaccinium corymbosum* L.

The novel variety of the *Vaccinium corymbosum* L. disclosed herein has been given the variety denomination: 'RYOKU NH-12'.

CROSS-REFERENCE TO RELATED APPLICATIONS

This application claims priority to Japanese Plant Breeders' Rights Application No. 31724, filed Jan. 4, 2017, the contents of which are incorporated herein by reference in their entirety.

BACKGROUND OF THE INVENTION

The present invention relates to a new and distinct hybrid variety of northern highbush blueberry (*Vaccinium corymbosum* L.) named 'RYOKU NH-12'. This novel variety was found by open pollination of 'Spartan', 'Duke' and 'Denies Blue' in the tests conducted for the period from 2004 to 2008 in Matsumoto-City, Nagano-prefecture, Japan. As stated below, 'RYOKU NH-12' has apparently different characteristics from those of the 'Spartan' and 'Duke', both being widely planted and important varieties in the Chubu district of Japan.

SUMMARY OF THE INVENTION

Blueberry variety 'RYOKU NH-12' exhibits outstanding and distinguishing characteristics when grown under normal horticultural conditions in the area from Nagano-prefecture to the north of the Kanto in Japan, including:

(1) more compact plant size;
(2) comparatively early fruit ripening time (50% fruit ripening around late June of each year in Matsumoto, Nagano, Japan);
(3) comparatively large and uniform fruit size;
(4) firmer and lower dehiscent fruits;
(5) sweeter fruits with better taste balance of sweetness and acidity; and
(6) better taste of fruits.

BRIEF DESCRIPTION OF THE DRAWINGS

The accompanying colored photographs (FIGS. 1 to 8) show typical bush, flower, fruit and leaf characteristics of the new *Vaccinium corymbosum* L. plant, 'RYOKU NH-12'. Colors shown are as accurate as can be reasonably reproduced by photographic means. In some cases, the color might differ slightly from the colors of 'RYOKU NH-12' recited in the description.

DETAILED BOTANICAL DESCRIPTION

A. Distinctive Characteristics of 'RYOKU NY-12'

Figure 1:
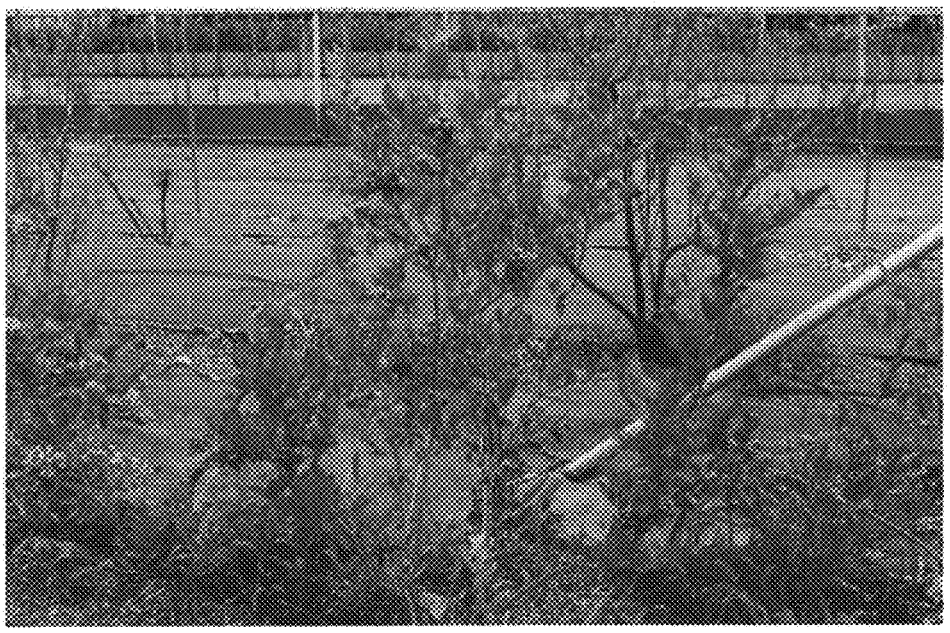
FIG. 1 shows a tree body of 'RYOKU NH-12' (photographed date: Jul. 9, 2014; photographed location: Matsumoto-City, Nagano-prefecture, Japan).
Figure 2:
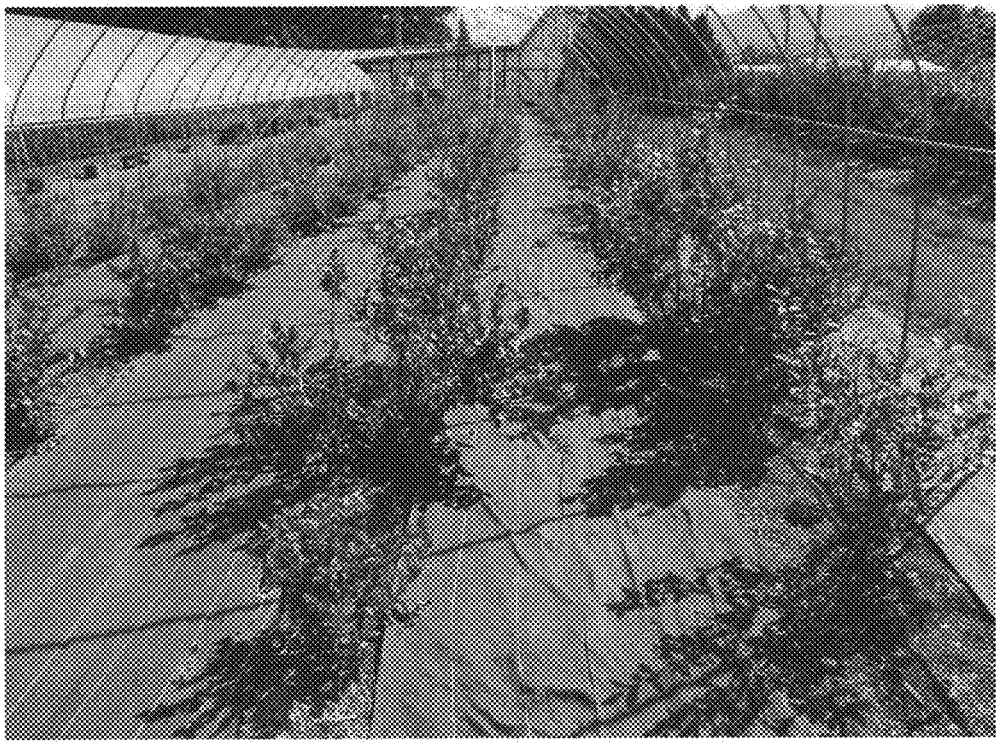
FIG. 2 shows a panoramic view of the cultivation area of 'RYOKU NH-12' (photographed date: Sep. 7, 2012; photographed location: same as FIG. 1).
Figure 3:
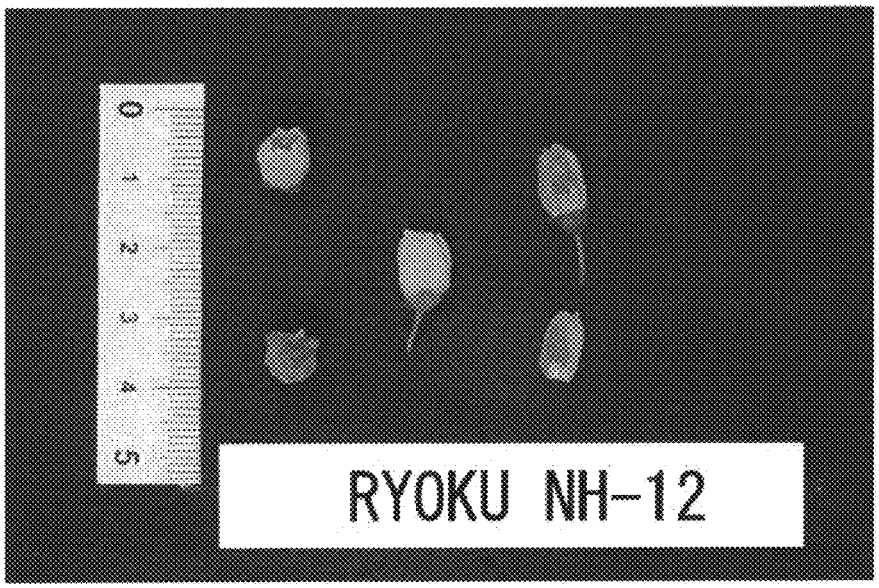
FIG. 3 shows whole flowers of 'RYOKU NH-12' (photographed date: May 6, 2014; photographed location: same as FIG. 1).
Figure 4:
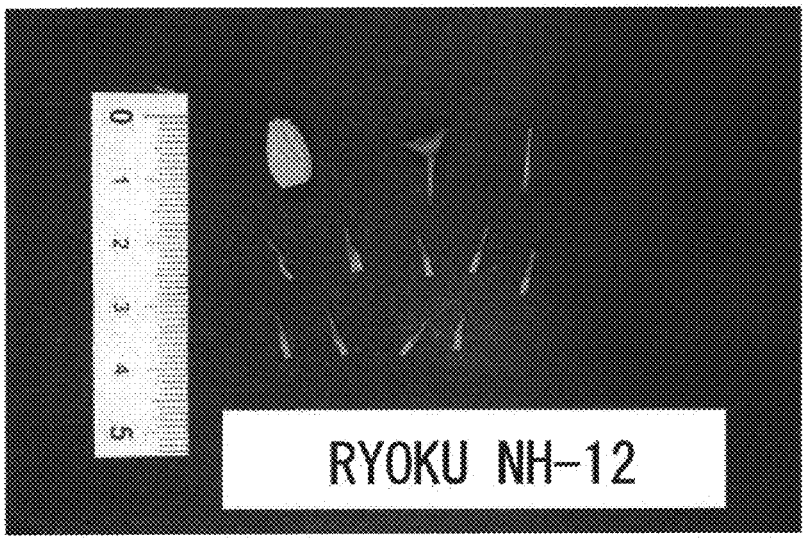
FIG. 4 shows broken-down parts of a flower of 'RYOKU NH-12' (photographed date: May 6, 2014; photographed location: same as FIG. 1).
Figure 5:
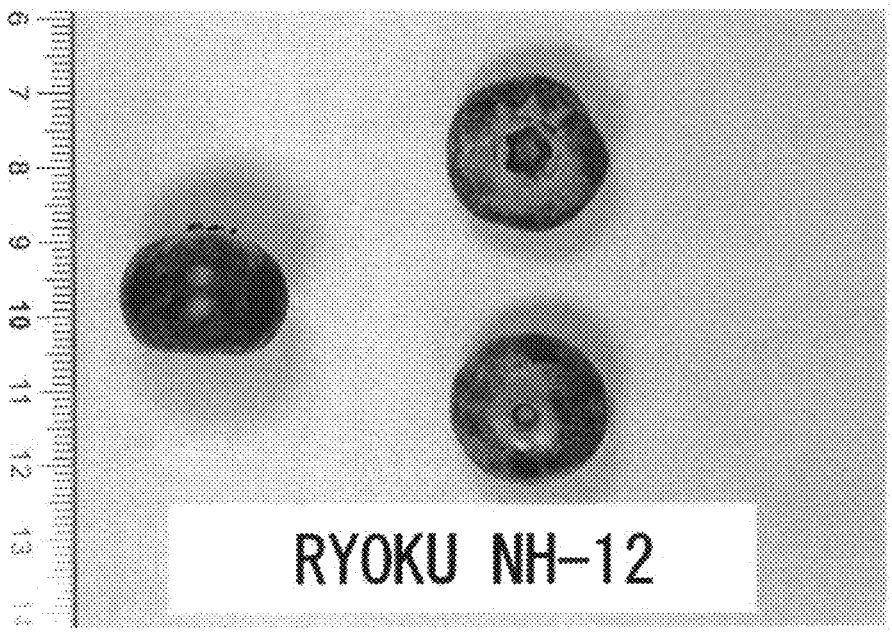
FIG. 5 shows fruits of 'RYOKU NH-12' (photographed date: Jul. 15, 2014; photographed location: same as FIG. 1).
Figure 6:
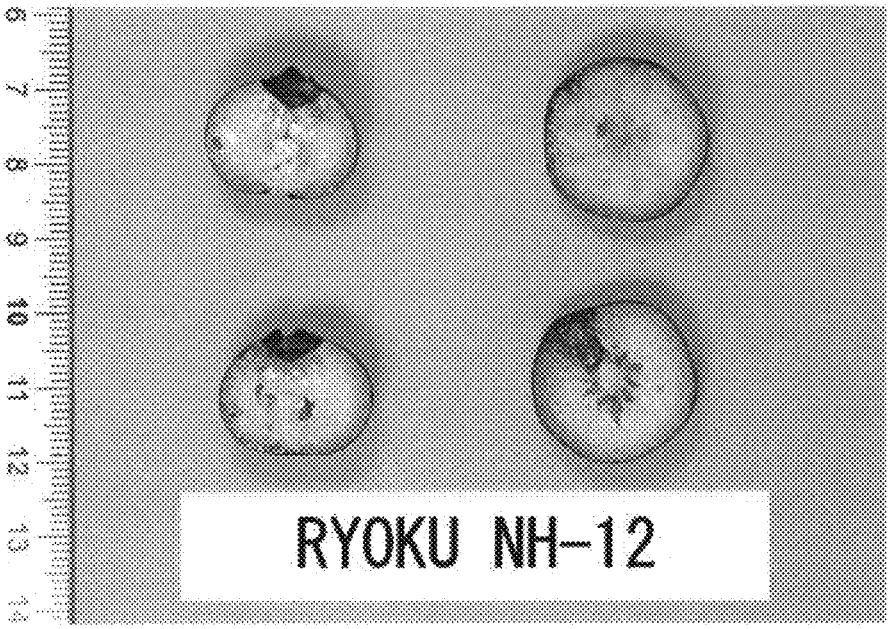
FIG. 6 shows a cross-section of the fruits of 'RYOKU NH-12' (photographed date: Jul. 15, 2014; photographed location: same as FIG. 1).
Figure 7:
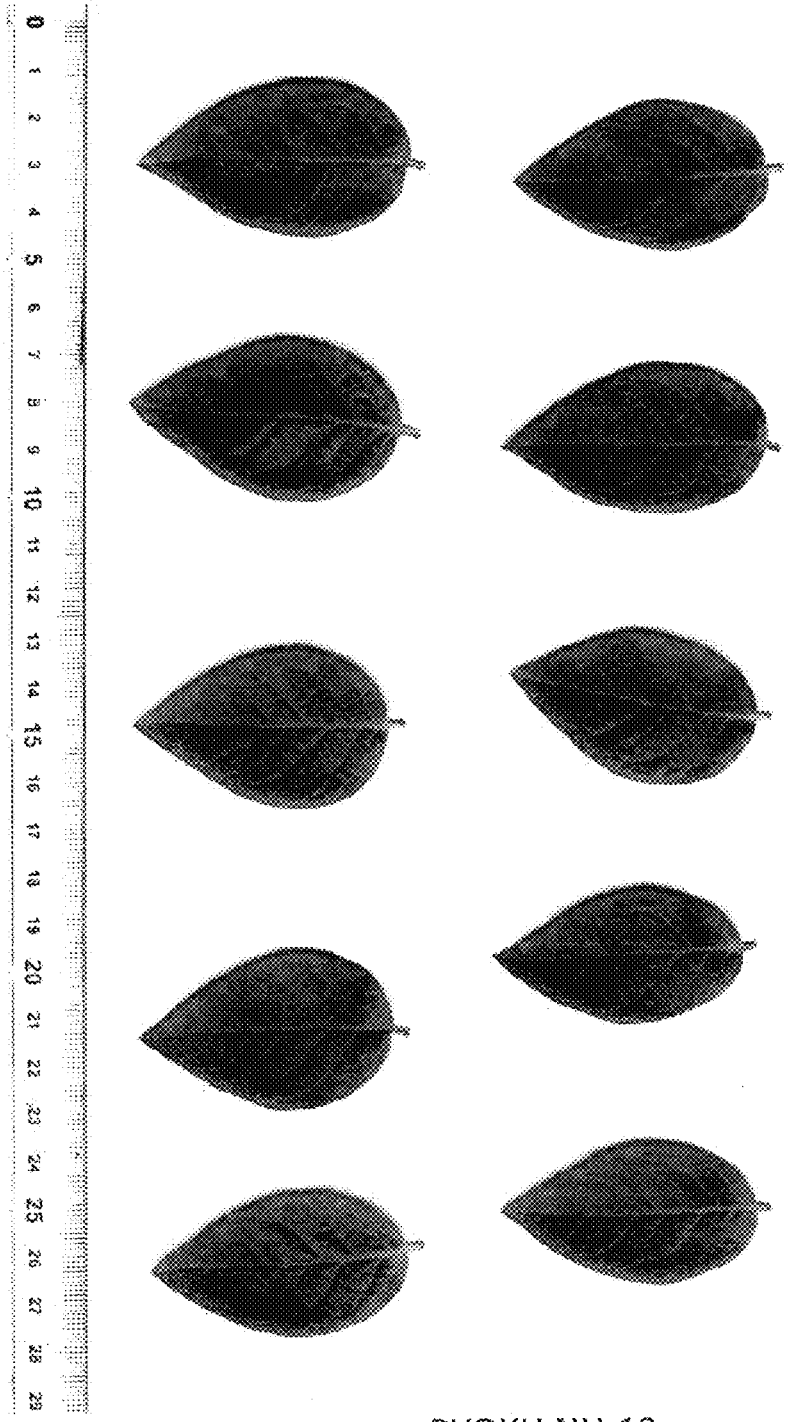
FIG. 7 shows an upper side of the leaves (10 sheets) of 'RYOKU NH-12' (photographed date: Aug. 3, 2012; photographed location: same as FIG. 1).
Figure 8:
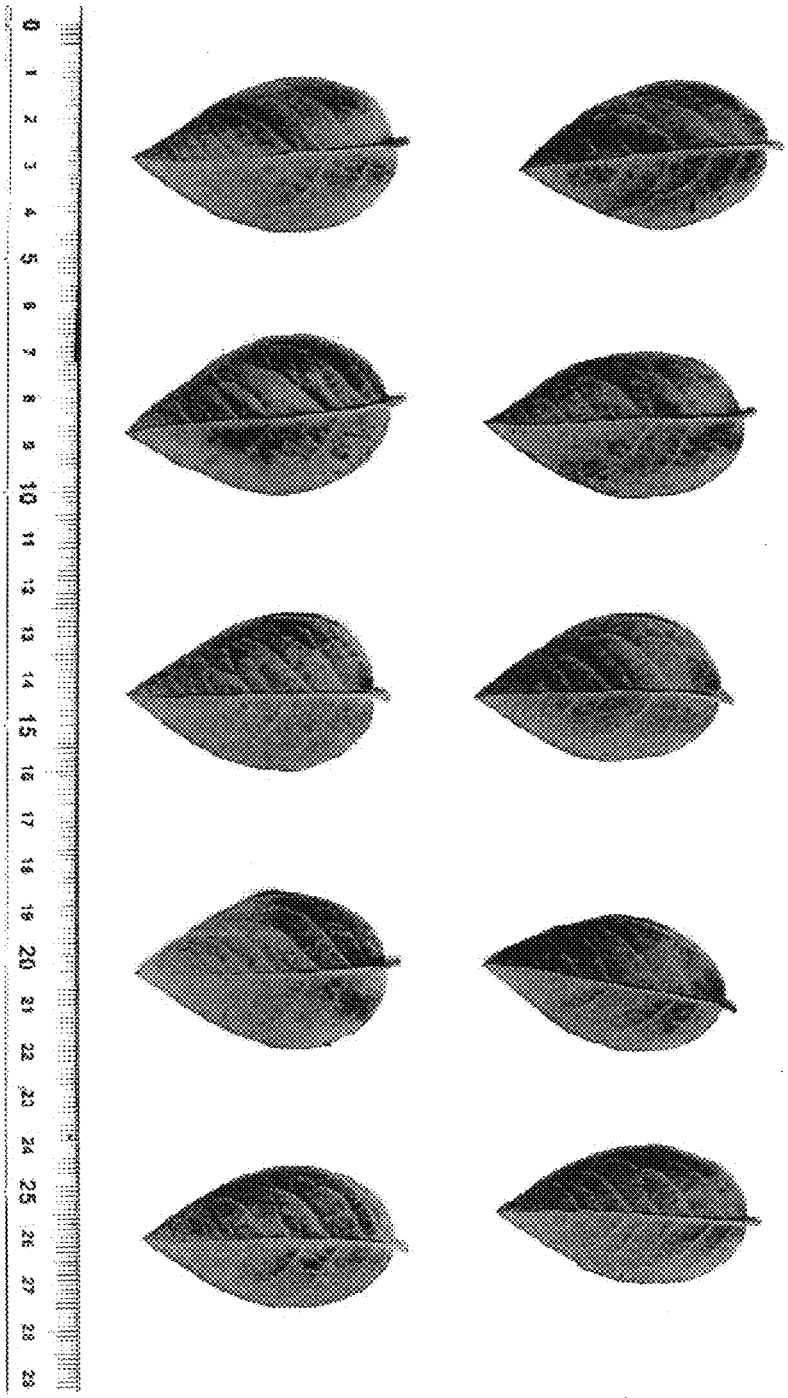
FIG. 8 shows a lower side of the leaves (10 sheets) of 'RYOKU NH-12' (photographed date: Aug. 3, 2012; photographed location: same as FIG. 1).

As described above, 'RYOKU NH-12' was obtained by the open pollination of 'Spartan', 'Duke' and 'Denies Blue'. On Apr. 15, 2004, about 1,000 seeds obtained from the mixed fruits of 'Spartan', 'Duke' and 'Denies Blue', all of which were harvested in a field in Matsumoto-City, Nagano-prefecture, Japan, seeded in plant seeding trays, and then transplanted to pots. The resulting seedlings (about 300) were planted in cultivation pots on May 1, 2005. Fructification of the planted seedlings was started from Jun. 20, 2008 (on Year 3), and about 20 plant individuals were selected based on the characteristics, including larger fruit size, better taste balance of sweetness and acidity, higher yield per plant, earlier ripening time, large and uniform fruits, etc. For the about 20 plant individuals selected, test plots (each including about 20 cuttings per plant individual) were formed, where these plants were asexually propagated by cutting means. During the period from Jul. 20, 2010 to Dec. 25, 2016 and for 3 generations, the plants were propagated and examined for their characteristics based on the growth, and yield and fruits quality in each test plot. For 10 test plots, the characteristics of the plants were observed for the period between the flowering time and the ripening time yearly for 4 years, and since neither variant nor off-type plant was observed for the period, the characterization of 'RYOKU NH-12' was finished on Dec. 25, 2016 and the breeding was completed.

'RYOKU NH-12' is a blueberry clone distinguishable from the important blueberry varieties 'Spartan' and 'Duke', both of which are widely planted in the Chubu district of Japan, due to its characteristics including more compact plant size, comparatively early fruit ripening time, comparatively large and uniform fruit size, firmer and lower dehiscent fruits, sweeter fruits with better taste balance of sweetness and acidity, and better taste fruits. 20 plants of 'RYOKU NH-12' had been propagated by cutting means in Matsumoto, Nagano, Japan, and all the resulting plants were phenotypically indistinguishable from the original plant variety 'RYOKU NH-12'. In addition, comparing to 'Spartan' and 'Duke', the claimed plant 'RYOKU NH-12' has more compact plant size, about 1 week earlier fruit ripening time (on average, around June 25 to July 1 of each year in Matsumoto, Nagano, Japan), larger and more uniform fruit size, and firmer and sweeter fruit when compared to its related variety 'Spartan', and has more compact plant size, lower dehiscent fruits, sweeter fruits, a better balance of sweetness and acidity, and better tasting of fruits when compared to the 'Duke' variety (see Table 1 below).

The following data defining characteristics of 'RYOKU NH-12' were collected from the asexual propagation carried out in Matsumoto, Nagano, Japan. The plant history was taken on a plot of 10 four-year-old plants growing in Matsumoto, Nagano, Japan. 'RYOKU NH-12' has not been observed under all possible environmental conditions, and the measurements provided might therefore vary if grown in different environments. Where averages are given, the sample size was 10.

B. Phenotypic Description of *Vaccinium corymbosum* L. ('RYOKU NH-12')

Characteristics of 'RYOKU NH-12' are further specifically described as follows:

1. Plant:
   - *Plant vigor*.—Medium.
   - *Growth habit*.—Semi-upright.
   - *Plant size*.—Small.
   - *Plant height*.—1.3 m on average for 4-year old plant.
   - *Plant spread*.—0.8 m on average for 4-year old plant.
   - *Color of bark of plant*.—Dark Red, 187-B (The R.H.S. Colour Chart).
   - *Cold hardiness*.—Survived in winter frost (below −10° C.) with minimum damage.
   - *Ease of propagation*.—Propagated from each of the dormant wood cutting and the softwood stem cutting, where the rooting percentage was greater than 70% and comparable to the other varieties.
2. Trunk and branches:
   - *Suckering tendency*.—Medium suckering tendency.
   - *Surface texture (of 6-month-old shoots)*.—Medium smoothness.
   - *Surface texture (of 3-year-old and older wood)*.—Medium smoothness.
   - *Color of new twigs observed in the field*.—Orangish yellow green.
   - *Internode length*.—16.2 mm on average.
3. Leaves:
   - *Length including petiole*.—54.0 mm on average.
   - *Width of leaf at widest point*.—33.0 mm on average.
   - *Shape*.—Ovate.
   - *Leaf margin*.—Entire.
   - *Color*.—Upper surface of leaves: Dark Yellowish Green, 139-A. Lower surface of leaves: Strong Yellow Green, 143-A (The R.H.S. Colour Chart).
   - *Pubescence*.—Upper Surface of leaves: Absent. Lower Surface of leaves: Absent. Margin: Absent.
   - *Timing of vegetative bud burst*.—Medium.
4. Flowers:
   - *Shape*.—Campanulate.
   - *Color of opened flower*.—Pale Yellow Green, 157-C (The R.H.S. Colour Chart).
   - *Flowering period*.—Mean date of 50% opening of flowers in Matsumoto-City, Nagano-prefecture, Japan is May 1 (2 days earlier than 'Spartan' variety).
   - *Corolla*.—Diameter: 7.4 mm on average. Length (from pedicel attachment point to corolla tip excluding the pedicel): 10.8 mm on average. Color: light green white. Anthocyanin coloration in corolla tube — Absent or very weak.
5. Reproductive organs:
   - *Pollen*.—Color: Yellow.
6. Fruit:
   - *Mean date of 50% harvest in Matsumoto-City, Nagano-prefecture*.—July 1 on average.
   - *Diameter of calyx aperture on mature berry*.—5.9 mm on average.

*Size and shape of calyx lobe on mature berry.*—Medium in size, outcurving, and having deep calyx basin.

*Detachment force for ripe berries* (*easy, medium, hard*).—Easy.

*Fruit cluster density* (*sparse, medium, dense*).—Medium.

*Fruiting type.*—On one-year old shoots only.

7. Berry:

*Cluster* (*tight, medium, loose*).—Medium.

*Weight* (*on well-pruned plants*).—3.79 g on average.

*Height.*—14.9 mm on average.

*Width.*—20.4 mm on average.

*Shape.*—Oblate.

*Skin of fruit, with bloom.*—Light Purplish Blue, 98-D (The R.H.S. Colour Chart).

*Intensity of fruit bloom.*—Medium.

*Skin of fruit, without bloom.*—Greyish Purplish Blue, 103-A (The R.H.S. Colour Chart).

*Immature berry color, with bloom.*—Medium green.

*Immature berry color, without bloom.*—Yellow green.

*Flesh color.*—Light Yellow Green, 150-D (The R.H.S. Colour Chart).

*Peel color.*—Medium blue.

*Color of seeds.*—Moderate Orange, N167-C (The R.H.S. Colour Chart).

*Pedicel scar.*—Medium. 2.92 mm on average.

*Firmness.*—Medium.

*Intensity of fruit sweetness.*—High, Bx 14.5.

*Intensity of fruit acidity.*—High, pH 2.59.

*Texture.*—Somewhat soft pulp, very juicy, medium seeds.

8. Use: 'RYOKU NH-12' produce northern highbush blueberries suitable for fruit-picking farms, fresh fruit markets and processed fruit market, etc.

9. Resistance to disease, insects, and mites: 'RYOKU NH-12' grew vigorously and showed excellent bush survival in the field. It appears to be tolerant to stem blight (*Botryosphaeria* spp.) and root rot (*Phytophthora cinnamoni*), with very few young plants dying soon after planting. The response of 'RYOKU NH-12' to the various fungal species that cause summer leaf spots is typical of other northern highbush varieties, and fungicide applications may be needed after harvest in order to reduce foliar diseases and to retain leaves until autumn and make maximum flower bud set. Similarly, susceptibility to typical blueberry insect and mite pathogens, such as spotted wing drosophila (*Drosophila suzukii*), blueberry gall midge (*Dasineura oxycoccana*) and blueberry bud mite (*Acalitus vaccini*), is similar to other northern highbush cultivars.

TABLE 1

(Comparison of characteristics among varieties)

| Charact. No. | UPOV No | Code | Characteristics | Definition |
|---|---|---|---|---|
| 1 | 1 (*) | QN (+) | Plant: vigor | Strength of growth level of plant |
| 2 | | QN | Plant: size | Size of plant crown |
| 3 | 2 (*) | QN G | Plant: growth habit | Whole shape of plant without pruning during dormant period |

TABLE 1-continued (Comparison of characteristics among varieties)

| | | | | |
|---|---|---|---|---|
| 4 | 3 | PQ | One-year-old shoot: color | Color of middle part of shoot extended before dormant period |
| 5 | | QN | One-year-old shoot: length | Length of middle part of shoot extended before dormant period |
| 6 | 4 | QN | One-year-old shoot: length of internode (upper half) | Length of internode of shoot extended before dormant period (upper half) |
| 7 | 5 (*) | QN | Leaf: length | Length of leaf sufficiently expanded |
| 8 | 6 | QN | Leaf: width | Maxiumum width of mature leaf |
| 9 | 7 | QN | Leaf: ratio legnth/width | Ratio of leaf length to maximum width (leaf length/ leaf width) |
| 10 | 8 (*) | PQ | Leaf: shape | Shape of mature leaf |
| 11 | | QN (+) | Leaf: shape of tip | Shape of tip of mature leaf |
| 12 | 9 | QL | Leaf: color of upper side | Color of surface of mature leaf |
| 13 | 10 (*) | QN | Only varieties with green leaf color : Leaf: intensity of green color on upper side | Intensity of green color on surface of mature leaf |
| 14 | 11 (*) | QL | Leaf: margin | Type of margin of mature leaf |
| 15 | 12 | QN | Flower bud: anthocyanin coloration | Intensity of anthocyanin coloration of flower bud occuring to one year old shoot |
| 16 | 13 | QN | Inflorescence: length (excluding peduncle) | Length of inflorescence at flowering time (excluding peduncle) |
| 17 | 14 | PQ | Flower: shape of corolla | Shape of corolla at full bloom |
| 18 | | PQ | Flower: color of corolla | Color of corolla at full bloom |
| 19 | 15 (*) | QN | Flower: size of corolla tube | Size of corolla tube at full bloom |
| 20 | 16 (*) | QN | Flower: anthocyanin coloration of corolla tube | Intensity of anthocyanin coloration on surface of corolla tube |
| 21 | 17 | QL | Flower: ridges on corolla tube | Presence or absence of ridges on corolla tube |
| 22 | 18 | QN | Fruit cluster: density | Density of fruit per fruit cluster |
| 23 | 19 (*) | QN | Unripe fruit: intensity of green color | Intensity of green color of fruit before ripening |
| 24 | 20 (*) | QN | Fruit: size | Size of fruit at ripening |
| 25 | 21 (*) | PQ (+) | Fruit: shape in longitudinal section | Shape in longitudinal section of fruit at ripening |
| 26 | | QN (+) | Fruit: size of scar | Size of stem scar of mature fruit |

TABLE 1-continued (Comparison of characteristics among varieties)

| | | | | |
|---|---|---|---|---|
| 27 | | PQ (+) | Fruit: shape of calyx cavity | Shape of calyx cavity of mature fruit |
| 28 | 22 | QN | Fruit: attitude of sepals | Attitude of sepals relative to mature fruit |
| 29 | 23 | QN | Fruit: type of sepals | Direction of curving of sepals |
| 30 | 24 | QN | Fruit: diameter of calyx basin | Diameter of calyx basin of mature fruit |
| 31 | 25 | QN | Fruit: depth of calyx basin | Depth of calyx basin of mature fruit |
| 32 | 26 (*) | QN | Fruit: intensity of bloom | Intensity of bloom on surface of mature fruit |
| 33 | 27 (*) | PQ G | Fruit: color of skin (after removal of bloom) | Color of skin of mature fruit after removal of bloom |
| 34 | 28 | QN (*) | Fruit: firmness | Firmness of mature fruit |
| 35 | | PQ | Fruit: color of flesh | Color of flesh of mature fruit |
| 36 | 29 (*) | QN (+) | Fruit: sweetness | Sweetness of mature fruit |
| 37 | 30 (*) | QN (+) | Fruit: acidity | Acidity of mature fruit |
| 38 | 31 (*) | QL G | Plant: fruiting type | Shoots to which fruit adnate |
| 39 | | QN | Fruit: tendency of cracking | Tendency of cracking during harvest season |
| 40 | 32 (*) | QN (+) | Time of vegetative bud burst | Time of beginning to burst first vegetative bud of each individual plant |
| 41 | 33 (*) | QN (+) G | Time of beginning of flowering on one-year-old shoot | Time of 10% flowering occuring to one year old shoot |

| Charact. No. | Method | Class | State | Standard Variety (Ex. Var.) |
|---|---|---|---|---|
| 1 | Observation (a) VG | 3 | weak | Bluetta, Meader |
| | | 5 | medium | Collins, Weymouth |
| | | 7 | strong | Berkeley, Homebell, Woodard |
| 2 | Observation (a) VG | 3 | small | Avonblue, Bluetta, Flordablue |
| | | 5 | medium | Bluecrop, Earliblue |
| | | 7 | large | Dixi, Homebell, Tifblue |
| 3 | Observation (a) VG | 1 | upright | Becyblue, Bluechip, June, Spartan |
| | | 2 | semi-upright | Bluecrop, Lateblue |
| | | 3 | spreading | Northland, Weymouth |
| 4 | Observation (a) VG | 1 | green | |
| | | 2 | greenish red | |
| | | 3 | greyish red | Briteblue, Homebell |
| | | 4 | reddish yellow | Berkeley, Dixi |
| | | 5 | reddish brown | Blueray, Darrow, Weymouth |
| | | 6 | dark red | |

TABLE 1-continued (Comparison of characteristics among varieties)

| | | | | |
|---|---|---|---|---|
| 5 | Measurement mm (a) VG | 3 | short | 5 |
| | | 5 | medium | |
| | | 7 | long | |
| 6 | Observation (a) VG | 3 | short | Avonblue, Weymouth |
| | | 5 | medium | |
| | | 7 | long | Jersey |
| 7 | Measurement mm (b) MS/VG | 3 | short | |
| | | 5 | medium | |
| | | 7 | long | |
| 8 | Measurement mm (b) MS/VG | 3 | narrow | |
| | | 5 | medium | |
| | | 7 | broad | |
| 9 | Measurement (b) MS/VG | 3 | small | |
| | | 5 | medium | |
| | | 7 | large | |
| 10 | Observation (b) VG | 1 | lanceolate | |
| | | 2 | ovate | Northland |
| | | 3 | elliptic | Berkeley, Collins, Coville |
| | | 4 | oblong | |
| 11 | Observation (b) VG | 3 | acute | Weymouth, Woodard |
| | | 5 | medium | Earliblue, Tifblue |
| | | 7 | obtuse | Berkeley, Climax, Southland |
| 12 | Observation (b) VG | 1 | yellow | |
| | | 2 | green | Bluechip, Bluecrop, Blueray |
| 13 | Observation (b) VG | 3 | light | |
| | | 5 | medium | |
| | | 7 | dark | |
| 14 | Observation (b) VG | 1 | entire | |
| | | 2 | serrate | |
| 15 | Observation (a) VG | 3 | weak | |
| | | 5 | medium | |
| | | 7 | strong | |
| 16 | Measurement mm (c) MS/VG | 3 | short | |
| | | 5 | medium | |
| | | 7 | long | |
| 17 | Observation (c) VG | 1 | urceolate | Bluecrop, Jersey |
| | | 2 | campanulate | Northblue, Northsky |
| | | 3 | cylindrical | |
| 18 | Observation (c) VG | 1 | white | Aliceblue, Bluetta, Briteblue |
| | | 2 | creamy white | Avonblue, Berkeley, Bluecrop |
| | | 3 | greenish white | Blueray, Collins, Coville |
| | | 4 | light pink | Bluebell, Delite, Dixi, Tifblue |
| 19 | Observation (c) VG | 3 | small | |
| | | 5 | medium | |
| | | 7 | large | |
| 20 | Observation (c) VG | 1 | absent or very weak | |
| | | 3 | weak | |
| | | 5 | medium | |
| | | 7 | strong | |
| 21 | Observation (c) VG | 1 | absent | Herbert |
| | | 9 | present | Aliceblue Berkeley, Dixi |

TABLE 1-continued (Comparison of characteristics among varieties)

| | | | | |
|---|---|---|---|---|
| 22 | Observation (d) VG | 3 | sparse | Homebell, Jersey, Woodard |
| | | 5 | medium | Bluechip, Bluecrop, Bluetta |
| | | 7 | dense | Darrow, Herbert, Patriot |
| 23 | Observation VG | 3 | light | |
| | | 5 | medium | |
| | | 7 | dark | |
| 24 | Observation (d) VG | 3 | small | Homebell, June, Northblue |
| | | 5 | medium | Collins, Earliblue |
| | | 7 | large | Berkeley, Bluecrop, Spartan |
| 25 | Observation (d) VG | 1 | elliptic | |
| | | 2 | round | Berkeley, Jersey, Sharpblue |
| | | 3 | oblate | Earliblue, Harrison, Woodard |
| 26 | Observation (d) VG | 3 | small | |
| | | 5 | medium | |
| | | 7 | large | |
| 27 | Observation (d) VG | 1 | star | |
| | | 2 | circular | |
| 28 | Observation (d) VG | 1 | erect | |
| | | 2 | erect to semi-erect | |
| | | 3 | semi-erect | |
| | | 4 | level | |
| 29 | Observation (d) VG | 1 | incurving | |
| | | 2 | straight | |
| | | 3 | reflexed | |
| 30 | Observation (d) VG | 3 | small | Avonblue, Bluechip, Sharpblue |
| | | 5 | medium | Blueray, Woodard |
| | | 7 | large | Coville, Darrow, Homebell |
| 31 | Observation (d) VG | 3 | shallow | Bluecrop, Rancocas, Tifblue |
| | | 5 | medium | Earliblue, Jersey |
| | | 7 | deep | Blueray, Collins, Dixi |
| 32 | Observation (d) VG | 1 | very weak | |
| | | 3 | weak | Dixi, Herbert, Sharpblue |
| | | 5 | medium | Collins, Coville |
| | | 7 | strong | Avonblue, Bluecrop, Tifblue |
| 33 | Observation (d) VG | 1 | light blue | Berkeley, Bluechip, Tifblue |
| | | 2 | medium blue | Blueray, Jersey, June |
| | | 3 | dark blue | Dixi, Homebell |
| | | 4 | blue red | |
| 34 | Observation (d) VG/VS | 3 | soft | Herbert, Homebell, Spartan |
| | | 5 | medium | Collins, Dixi |
| | | 7 | firm | Coville, Southland |
| | | 9 | very firm | |

TABLE 1-continued (Comparison of characteristics among varieties)

| | | | | |
|---|---|---|---|---|
| 35 | Observation (d) VG | 1 | white | Berkeley, Bluecrop, Blueray |
| | | 2 | cream | Earliblue |
| | | 3 | light green | Bluechip, Lateblue, Sharpblue |
| | | 4 | light purple | Aliceblue, Delite, Homebell |
| 36 | Observation (d) VG | 3 | low | Avonblue, Bluechip |
| | | 5 | medium | Berkeley, Bluetta, Spartan |
| | | 7 | high | Aliceblue, Bluecrop, Blueray |
| 37 | Observation (d) VG | 3 | low | Earliblue, Homebell |
| | | 5 | medium | Blueray, Herbert |
| | | 7 | high | Collins, Elliott, Lateblue |
| 38 | Observation (c) VG | 1 | on one-year-old shoots only | |
| | | 2 | on one-year-old and current season's shoots | |
| 39 | Observation (d) VG | 3 | less | Earliblue, Herbert, Spartan |
| | | 5 | medium | Avonblue, Berkeley, Bluechip |
| | | 7 | much | Briteblue, Climax, Darrow |
| 40 | Measurement MG | 3 | early | Avonblue, Beckyblue Sharpblue |
| | | 5 | medium | Darrow, Weymouth |
| | | 7 | late | Elliot, Lateblue |
| 41 | Measurement MG | 1 | very early | |
| | | 3 | early | |
| | | 5 | medium | Bluecrop, Collins, Woodard |
| | | 7 | late | Dixi, Herbert, Lateblue |
| | | 9 | very late | |

| Charact. | The present variety RYOKU | Control Varieties | |
|---|---|---|---|
| No. | NH-12 | Spartan | Duke |
| 1 | 5 | 6 | 7 |
| 2 | 3 | 5 | 7 |
| 3 | 2 | 1 | 2 |
| 4 | 5 | 4 | 4 |
| 5 | 7 (164 mm) | 7 (222 mm) | (245 mm) |
| 6 | 4 (16.2 mm) | 5 (17.0 mm) | 5 (18.0 mm) |
| 7 | 3 (54.0 mm) | 5 (76.0 mm) | 5 (71.0 mm) |
| 8 | 5 (33.0 mm) | 5 (37.0 mm) | 5 (36.0 mm) |
| 9 | 4 (1.64) | 5 (2.05) | 5 (1.97) |
| 10 | 2 | 3 | 3 |
| 11 | | | |
| 12 | 2 | 2 | 2 |
| 13 | 5 | 7 | 7 |
| 14 | 1 | 1 | 1 |
| 15 | 5 | 5 | 5 |
| 16 | 7 (35.7 mm) | 5 (25.2 mm) | 5 (26.4 mm) |
| 17 | 2 | 1-2 | 2 |
| 18 | 2 | 2-3 | 2-3 |

TABLE 1-continued (Comparison of characteristics among varieties)

| | | | |
|---|---|---|---|
| 19 | 5 | 5 | 6 |
| 20 | 1 | 1 | 3 |
| 21 | 9 | 9 | 9 |
| 22 | 5 | 5 | 5 |
| 23 | 5 | 3 | 5 |
| 24 | 7 | 7 | 7 |
| | (3.79 g) | (4.56 g) | (3.96 g) |
| 25 | 3 | 3 | 3 |
| 26 | 5 | 5 | 5 |
| | (2.92 mm) | (2.30 mm) | (1.90 mm) |
| 27 | 2 | 2 | 2 |
| 28 | 2 | 1 | 1 |
| 29 | 3 | 1 | 3 |
| 30 | 5 | 5 | 5 |
| | (5.86 mm) | (5.80 mm) | (5.90 mm) |
| 31 | 7 | 7 | 5 |
| | (2.72 mm) | (2.20 mm) | (1.50 mm) |
| 32 | 5 | 5 | 5 |
| 33 | 2 | 2 | 2 |
| 34 | 5 | 3 | 5 |

TABLE 1-continued (Comparison of characteristics among varieties)

| | | | |
|---|---|---|---|
| 35 | 1 | 2-3 | 1-2 |
| 36 | 7 | 5 | 5 |
| | (Bx 14.5) | (Bx 11.9) | (Bx11.1) |
| 37 | 7 | 5 | 3 |
| | (pH 2.59) | (pH 3.12) | (pH 3.87) |
| 38 | 1 | 1 | 1 |
| 39 | 3 | 3 | 5 |
| 40 | 5 | 7 | 5 |
| | Apr. 6, 2016 | Apr. 8, 2016 | Apr. 5, 2016 |
| 41 | 3 | 3 | 3 |
| | Apr. 25, 2016 | Apr. 24, 2016 | Apr. 24, 2016 |

What is claimed is:

1. A new and distinct variety of *Vaccinium corymbosum* L. plant named 'RYOKU NH-12', as described and illustrated herein.

* * * * *

RYOKU NH-12

RYOKU NH-12